(12) United States Patent
Cummins

(10) Patent No.: US 7,804,309 B2
(45) Date of Patent: Sep. 28, 2010

(54) SYSTEMS AND METHODS FOR SOIL MOISTURE ESTIMATION

(75) Inventor: Kenneth L. Cummins, Tucson, AZ (US)

(73) Assignee: Vaisala OYJ, Helsinki (FI)

( * ) Notice: Subject to any disclaimer, the term of this patent is extended or adjusted under 35 U.S.C. 154(b) by 375 days.

(21) Appl. No.: 11/953,005

(22) Filed: Dec. 7, 2007

(65) Prior Publication Data
US 2008/0143350 A1 Jun. 19, 2008

Related U.S. Application Data

(60) Provisional application No. 60/873,629, filed on Dec. 7, 2006.

(51) Int. Cl.
*G01R 27/04* (2006.01)
(52) U.S. Cl. .................. 324/694; 324/637; 324/640; 324/643; 324/329
(58) Field of Classification Search ............ 324/694, 324/72, 637, 640, 643, 329, 330, 332–335
See application file for complete search history.

(56) References Cited

U.S. PATENT DOCUMENTS

| | | | |
|---|---|---|---|
| 3,398,356 A * | 8/1968 | Still .......................... | 324/338 |
| 3,763,419 A | 10/1973 | Barringer | |
| 6,735,525 B1 | 5/2004 | Murphy | |

OTHER PUBLICATIONS

Pellerin L. et al.; "Multi-dimensional electromagnetic modeling and inversion with application to near-surface earth investigations", Computer and Electronics in Agriculture; Elsevier; vol. 46, No. 1-3; Mar. 2005; pp. 71-102, XP004752228.
Chaplot V. et al.; "Mapping field-scale hydromorphic horizons using Radio-MT electrical resistivity"; Geoderma, vol. 102, No. 1-2; Jul. 2001; pp. 61-74, Elsevier; XP002477454.
Corwin D. L. et al.; "Apparent soil electrical conductivity measurements in agriculture"; Computers and Electronics in Agriculture, vol. 46, No. 1-3; Mar. 2005; pp. 11-43; Elsevier: XP004752226.
"IEEE guide for radio methods of measuring each conductivity"; Report No.; IEEE STD 356-1974 Inst. Electr. Electron. Eng.; Feb. 20, 1974; pp. 1-32; New York, NY, USA; XP002477455.

(Continued)

*Primary Examiner*—Vincent Q Nguyen
(74) *Attorney, Agent, or Firm*—Allen J. Moss; Lucius L. Lockwood; Squire, Sanders & Demspey L.L.P.

(57) ABSTRACT

Embodiments of the present invention provide estimates of soil moisture by measuring the change in electrical conductivity near the surface of the earth using surface-propagated electromagnetic fields. A method is provided for estimating near-surface soil moisture, including measuring signals from an electromagnetic ground wave propagating between one or more receiving element locations, determining a transfer characteristic proportional to an average electrical conductivity between pairs of locations; and determining estimated soil moisture in one or more regions derived from analyzing the determined electrical conductivity between pairs of locations and a predetermined regional relationship between electrical conductivity and soil moisture.

44 Claims, 8 Drawing Sheets

OTHER PUBLICATIONS

Tezkan, Bulent: "A review of Environmental applications of quasi-stationary electromagnetic techniques"; Surveys in Geophysics; vol. 20, 1999; pp. 279-308; Netherlands; XP002477456.

Divya et al.; "Parallel and perpendicular electric field components of a lightning discharge"; Geoexploration; vol. 23, No. 2; Jun. 1985; pp. 227-237; Elsevier; Netherlands; XP002477457.

Moini R. et al.; "Analysis of lightning-radiated electromagnetic fields in the vicinity of lossy ground"; IEEE Transactions on Electromagnetic Compatibility; vol. 47, No, 1; Feb. 2005; IEEE Service Center; New York, NY, USA; XP011127083.

Schueler J. R. et al.; "Estimating ground conductivity and improving lightning location goodness of fit by compensating propagation effects"; Radio Science American Geophys. Union USA; vol. 41, No. 1; Jan. 2006; p. 13; XP009099024.

Pettinelli E. et al.; "Early-time GPR signal analysis: implications for water content measurement"; Advanced Ground Penetrating Radar, 2005; IWAGPR 2005; Proceedings of the 3rd International Workshop on DELFT: May 2-3, 2005; pp. 51-54, IEEE, NJ, USA; XP010824048.

Klysz G. et al.; "Spectral analysis of radar surface waves for non-destructive evaluation of cover concrete"; NDT & E International, vol. 37, No. 3; Apr. 2004; pp. 221-227, Oxford, GB; XP0044960139.

Database WPI Week 198502; Derwent Publications Ltd.; London GB; AN 1985-010675; SU 1093293 A; May 23, 1984; XP002477459.

Stokke K. N.; Database Inspec [online]; "Measurements of signals from a radio beacon. Influence of the ground conductivity"; The Institution of Electrical Engineers; 1988; XP002477458.

Johler J.R. et al., "Ground-Conductivity Determinations at Low Radio Frequencies by an Analysis of the Steric Signatures of Thunderstorms," Central Radio Propagation Laboratory, National Bureau of Standards, Boulder, Colorado, Journal of Geophysical Research, vol. 66, No. 10, Oct. 1961, pp. 3233-3244.

William D. Scheftic et al., "Wide-Area Soil Moisture Estimation Using the Propagation of Lightning Generated Low-Frequency Electromagnetic Signals," 2008 20th International Lightning Detection Conference, Apr. 21-23, Tucson, Arizona; 2nd International Lightning Meterology Conference, Apr. 24-25, Tucson, Arizona, pp. 1-8.

Edward A. Bardo et al., "Lightning Current Parameters Derived from Lightning Location Systems; What Can We Measure?" ILDO 2004, Ref. No. 39, 18th International Lightning Detection Conference, Jun. 7-9, Lelsinki, Finland, pp. 1-13 6/2004.

S.O. Bashir, "Determination of Ground Conductivity in Bahrain by the Ground-Wave Attenuation Method," University of Bahrain, Bahrain, pp. 466-468 Mar. 30, 1993.

* cited by examiner

SYSTEMS AND METHODS FOR SOIL MOISTURE ESTIMATION

CROSS REFERENCE TO RELATED APPLICATIONS

This application is related to and claims priority from U.S. provisional patent application No. 60/873,629, filed Dec. 7, 2006 and entitled "Systems And Methods For Soil Moisture Estimation Using Broadband, Low-Frequency Electromagnetic Signals," the disclosure of which is fully incorporated by reference herein for all purposes.

BACKGROUND OF THE INVENTION

1. Field of the Invention

The present invention relates to measurement and characterization of soil moisture content, and more particularly, to methods and systems for using electromagnetic radiation to determine soil moisture content over a large geographic area.

2. Description of the Related Art

Land surface moisture measurements are central to our understanding of the earth's water system. Among many potential applications, accurate and up-to date knowledge of surface moisture content enables more accurate model-based weather/climate predictions, and assists with management of weather-related phenomena such as flash flood forecasting. Further, knowledge of surface moisture variation has numerous agricultural applications, such as assisting with more effective crop management and drought monitoring.

While small-scale local soil moisture measurement systems have been developed, there is a clear need for improved soil moisture estimates on both regional and continental scales. Particularly missing in prior applications are methods or systems for obtaining continuous, wide-area, near-surface (5-200 cm) water storage measurements. This is exemplified by the fact that the North American Land Data Assimilation System (NLDAS) relies on multiple models driven by meteorological data to extrapolate water storage, but the extrapolated results from these models are not in good agreement.

Several techniques have been used in the past to obtain soil moisture estimates. One approach includes the use of local probes to measure soil moisture at fixed positions. This is impractical for wide-area coverage. Also, since the rainfall rates in convective storms vary significantly over distances of a few kilometers, soil moisture estimates derived from point measurements may not accurately reflect broad regional conditions. Wide-area estimates can be derived by coupling rainfall estimates and hydrological models, but both the models and the rainfall estimates are poor, and lead to extremely large errors. Currently, space-based passive microwave measurements provide an alternative option, but even this approach suffers from limited penetration depth and/or signal attenuation due to vegetation. Also, there are currently no plans for continuous geostationary satellite monitoring of land surface moisture, at least over North America. Therefore, there is a need for improved systems and methods to obtain wide-area, continuous soil moisture estimates.

SUMMARY OF THE INVENTION

There are presented systems and methods for soil moisture estimation. Aspects of the present invention demonstrate the potential to use surface-propagated Low-Frequency (LF) and Medium-Frequency (MF) electromagnetic signals to infer changes in near-surface (approximately 1 meter) water storage. More specifically, aspects of the present invention show that the rise times of propagated electromagnetic field waveforms produced by cloud-to-ground (CG) lightning are very sensitive to changes in surface conductivity associated with changes in soil moisture. The present invention may employ both lightning and man-made transmitter sources (in the LF and MF frequency ranges) in order to provide continuous soil moisture estimates. The resulting instrumentation and methods may be used to produce continuous (e.g., approximately hourly) wide-area (such as continental-scale) soil moisture information, and to provide this information as part of a commercial data service. In certain embodiments, systems and methods consistent with the present invention may be better able to estimate changes in soil moisture than absolute soil moisture.

In one embodiment, a method is disclosed for estimating near-surface soil moisture, the method comprising: measuring signals from an electromagnetic ground wave propagating between two or more receiving element locations; determining a transfer characteristic proportional to the average electrical conductivity between pairs of locations; and determining estimated soil moisture in one or more regions derived from analyzing the determined electrical conductivity between pairs of locations and a predetermined regional relationship between electrical conductivity and soil moisture. The electromagnetic wave may be produced by cloud-to-ground lightning. In this and other embodiments, the transfer characteristic is derived from waveform parameters in the frequency domain or a plurality of time-domain parameters, and is determined from rising edge characteristics of the signals. In an embodiment, the time-domain parameters include at least one of a peak amplitude, a time delay, and a rise time of the signals.

In another embodiment, a method is provided for estimating near-surface soil moisture, the method comprising: measuring signals from an electromagnetic ground wave produced by one or more man-made narrowband transmitters in the frequency range of 30 kHz to 5 MHz at two or more receiving element locations; determining a transfer characteristic, proportional to the average electrical conductivity between pairs of locations; and determining estimated soil moisture in one or more regions derived from the determined electrical conductivity between pairs of locations and knowledge of the regional relationship between electrical conductivity and soil moisture. In various embodiments, the transfer characteristic is derived from waveform parameters in the time domain. In an embodiment, the time-domain parameters include at least one of a peak amplitude and a phase delay. The transfer characteristic may also be derived from waveform parameters in the frequency domain.

In yet another embodiment, a method for estimating near-surface soil moisture is provided, the method comprising: measuring signals from an electromagnetic ground wave produced by one or more return strokes of cloud-to-ground lightning from at least one receiving element location; determining a transfer characteristic proportional to the average electrical conductivity between the locations of the lightning and one or more receiving elements; determining estimated soil moisture in one or more regions derived from the determined electrical conductivity between a lightning strike location and at least one receiving element location and knowledge of the regional relationship between electrical conductivity and soil moisture. In this and other embodiments, the transfer characteristic is derived from waveform parameters in the frequency domain or a plurality of time-domain parameters, and is determined from rising edge characteristics of the signals. In an embodiment, the time-domain parameters include at least one of a peak amplitude, a time delay, and a rise time of the signals.

In another embodiment, there is presented a method for estimating near-surface soil moisture, the method comprising: synthesizing a broadband signal for propagation as a ground wave; transmitting the synthesized signal from a transmitting element location as an electromagnetic wave coupled to a ground propagation medium at known times; measuring one or more received signals at one or more receiving element locations; determining a transfer characteristic proportional to an average electrical conductivity between pairs of locations; and determining estimated soil moisture in one or more regions derived from (a) the determined electrical conductivity between the transmitting element location and at least one receiving element location and (b) knowledge of the regional relationship between electrical conductivity and soil moisture. The transfer characteristic may be derived from waveform parameters in the time domain, and the waveform parameters may include at least one of a peak amplitude and a phase delay for at least one frequency. Also, the transfer characteristic may be derived from waveform parameters in the frequency domain. A set of vectors representing a broadband test signal may be generated, and appropriately formatted for presentation to an input of a transmission source. In certain embodiments, the time of transmission of the synthesized signal may not be not precisely known and two or more receiving elements may be employed. In additional embodiments, the broadband signal comprises a pseudorandom noise signal, or a broadband Gaussian noise signal. The broadcast of the broadband signal may be controlled, for example, by specifying at least one of an initial broadcast time, and ending broadcast time, a broadcast repeat interval, or a number of broadcast repetitions.

There is also provided in an embodiment a soil moisture monitoring system comprising: a data collection and management component coupled to one or more RF receiving elements respectively located at one or more receiving element locations; and an input archive; and a central processing component coupled to the data collection and management component; a product generator; and an output archive; and a memory coupled to the processing component and storing instructions that, when executed, cause the processing component to obtain signals measured from an electromagnetic wave propagating as a ground wave between a transmitter and at least one receiving element location; determine a transfer characteristic proportional to an average electrical conductivity between the transmitter and at least one receiving element; and determine estimated soil moisture in one or more regions derived from analyzing the determined electrical conductivity between pairs of locations and a predetermined regional relationship between electrical conductivity and soil moisture. Each of the one or more RF receiving element locations are separated from a each other by a predetermined minimum distance, and in one embodiment, the predetermined minimum distance is 1 kilometer. In an additional embodiment, the data collection and management component is further coupled to (a) an RF transmission source comprising the transmitter; and (b) an input generator that is also coupled to the data collection and management component, the input generator being configured to create data for presentation to inputs of the RF transmission source. The transmission source may further comprise one or more transmitting elements that transmit signals at one or more frequencies that can propagate as a ground wave, and in this embodiment, the transfer characteristic may be derived from waveform parameters in the time domain such as a peak amplitude and a phase delay, or may be derived from waveform parameters in the frequency domain.

In an alternate implementation, the above-referenced soil moisture monitoring system further comprises a transmission source including RF energy produced by one or more return strokes of cloud-to-ground lightning, and the transfer characteristic is derived from waveform parameters in the time domain. In this implementation, a plurality of time-domain parameters is determined from rising edge characteristics of the signals including at least one of a peak amplitude, a time delay, and a rise time of the signals, or the transfer characteristic may be derived from waveform parameters in the frequency domain.

In yet another implementation of the above-referenced system, the electromagnetic wave includes RF sources such as AM, LORAN, ATC directional beacons, man-made sources of broadband electromagnetic energy, and combinations of those source types. In this implementation, the transfer characteristic is derived from waveform parameters in the time domain, and the parameters may include at least one of a peak amplitude and a phase delay. The transfer characteristic may also be derived from waveform parameters in the frequency domain.

It is to be understood that both the foregoing general description and the following detailed description are exemplary and explanatory only and are not restrictive of the invention, as claimed.

The accompanying drawings, which are incorporated in and constitute a part of this specification, illustrate several embodiments of the invention and together with the description, serve to explain the principles of the invention.

BRIEF DESCRIPTION OF THE DRAWINGS

Reference will now be made in detail to the present exemplary embodiments of the invention, examples of which are illustrated in the accompanying drawings. Wherever possible, the same reference numbers will be used throughout the drawings to refer to the same or like parts.

DESCRIPTION OF THE EMBODIMENTS

Figure 1:
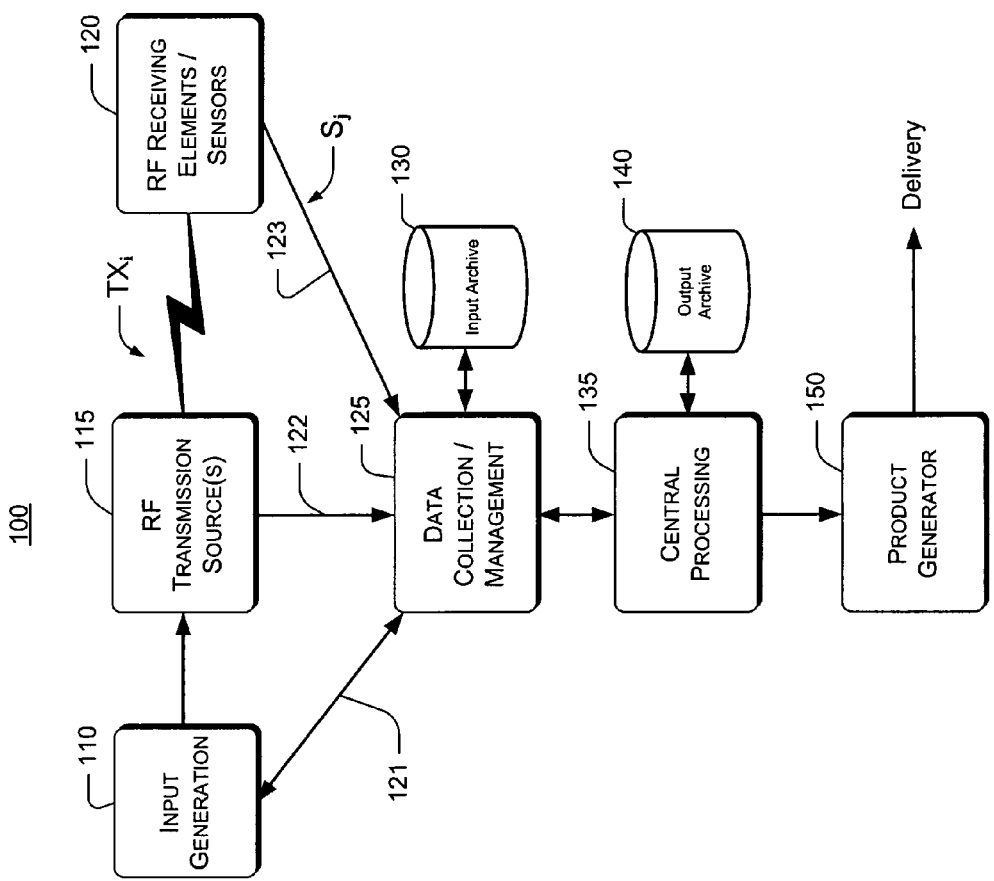
FIG. 1 illustrates a block diagram of an embodiment of the soil moisture measurement system.

Embodiments of the present invention provide estimates of soil moisture by measuring the change in electrical conductivity near the surface of the earth using surface-propagated electromagnetic fields. Turning to FIG. 1, an exemplary system 100 of the present invention is presented. An RF transmission source 115 comprises one or more transmitting elements that transmit signals at one or more frequencies that can propagate as a ground wave, e.g., 30 kHz to 5 MHz (shown as $TX_i$). In one embodiment, the transmitting elements may include man-made RF sources such as AM, LORAN, ATC directional beacons, or other appropriate man-made sources of electromagnetic energy. Optionally, an input generator 110 creates data, signals or vectors of data that may be provided to the inputs of a transmission source 115, or in another embodiment, the input that is provided to the transmission source is included in characteristics of an RF source such as a lightning strike. The propagated signals $TX_i$ are received at one or more RF receiving elements or sensors 120, separated from the transmitting element(s) and each other by an appropriate distance, (e.g., at least several kilometers), and the received signals $S_j$ are relayed to a centralized data collection/management component 125. The data collection component 125 is also linked to the optional input generator 110, and the RF transmission source 115, so that all data and signals involved in the generation, transmission, and measurement of propagated RF signals may be stored in an input archive 130 for additional retrieval and/or analysis. The data collection and management element 125 relays information to a central processing system 135 that collects and processes the information, resulting in information products that may be delivered by a product generator component 150. Processed information to be used by the product generator is stored in the output archive 140.

In various embodiments, the transmitting elements 115 may be either cloud-to-ground (CG) lightning discharges, broadband LF/MF signals, or narrow-band emissions produced by man-made transmitting sources, such as navigation signals or other radio emissions in the LF and MF ranges. The receiving elements 120 may be either broadband sensors, such as those employed for lightning detection, or are narrow-band receivers designed to operate at desired frequencies. The narrow-band receivers can either have a fixed operating frequency or can employ an adjustable operating frequency. The central processing system 135 may determine the differences in signal characteristics among the transmitter signals $TX_i$ and the signals received by the sensors $S_j$, and thus determine the average electrical conductivity of the path between these elements. The central processing system 135 may then convert the electrical conductivity to an estimate of the percent moisture saturation of the soil, based on regionally-specific conversion tables produced by modeled and/or measured relationships.

Since CG lightning is associated with thunderstorms that also produce convective precipitation, high-power LF electromagnetic fields produced by lightning may be used to "probe" soil moisture (based on surface electrical conductivity changes). Many regions receive more than half of their rainfall from convective storms that produce lightning and significant changes in soil moisture.

Thunderstorms are not present in all locations at all times, therefore embodiments of the present invention provide for several alternate types of electromagnetic signals that may be used to "probe" changes in soil moisture. For example, but not by way of limitation, the U.S. FCC has demonstrated that AM radio signals can be employed to infer soil conductivity over wide areas. However, the technique employed by the FCC is not amenable to continuous monitoring of changes in soil electrical conductivity produced by changes in soil moisture, and does not allow inference of soil moisture from the conductivity measurements.

Some advantages of aspects of the present invention over existing satellite-based methods for estimating soil moisture include: (1) minimal disturbance by terrain variation due to signal wavelengths in the range of 1-3 kilometers, (2) penetration depth of more than a meter, (3) signals propagate over a long distance of earth surface, (4) minimal effect of changes in vegetation, (5) high density of man-made "probes" (LORAN, NDB, AM, . . . ) and (6) continuous moisture monitoring (no orbit-based sampling).

In one implementation, the communications links 121, 122 allow the transmission of low-rate digital information (command and control) to the input generators 110 and the transmission sources 115. In addition to command and control functionality, link 123 provides sufficient bandwidth to transfer waveform information from the receiving sensors 120 to the data collection component 125 in a timely manner (e.g. within a few minutes).

Acceptable communications include, but are not limited to, digital cellular (CDMA) communications (~64-128 kbps) or 2-way satellite (VSAT) communications (~9.6-38.4 kbps).

In one embodiment, the sensors 120 may comprise antenna elements responsive to electric or magnetic fields in the frequency range of 30 kHz to 5 MHz (or a subset of this range), a signal amplifier, a signal processing subsystem, and a communications interface. The signal processing subsystem is time-synchronized to a reference clock to allow identification and processing of time-matched signals by the central processing system. The sensor's signal processing subsystem may process either analog or digital signals representative of the electric or magnetic field waveforms. In a preferred embodiment, a digital processing is employed comprising a 5 MHz 14-bit ADC and FPGA-based signal processing. A digital clock synchronized to GPS with an accuracy of 20 nSec RMS is utilized for sampling and time-stamping the signals. The information extracted during signal processing is either a short-duration waveform of interest (requiring further processing at the central processor), transient waveform features, or narrow-band signal properties at desired frequencies, as described further below.

The central processing system 135 will periodically (every few minutes) receive, store, and processes information provided by the sensors 120, using one or more of the methods described below.

Figure 2:
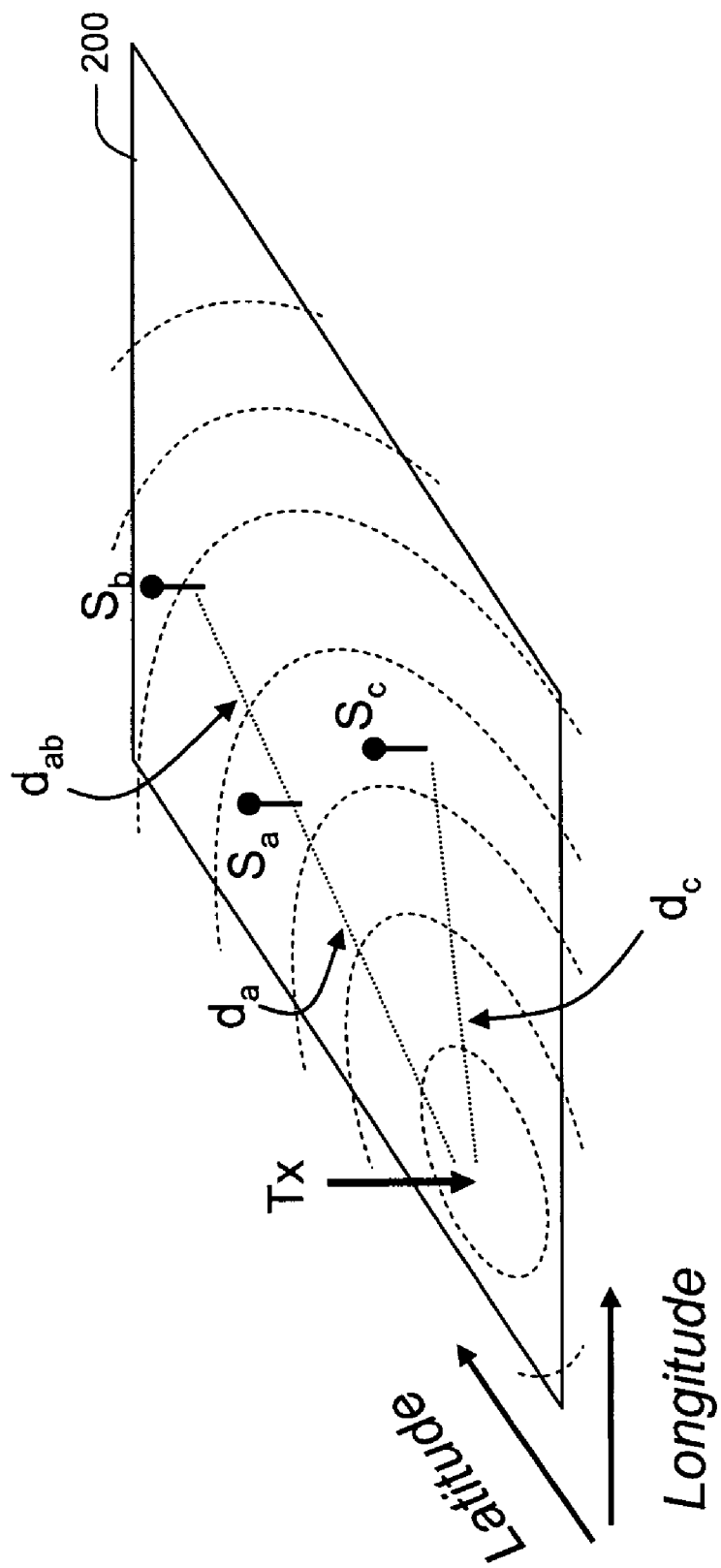
FIG. 2 illustrates an example process for measurement of soil moisture, shown in the context of a section of land to be characterized.

An application of a general measurement and processing method of the present invention is illustrated in FIG. 2. A transmitting element (shown at Tx) is located several kilometers away from one or more receiving elements ($S_a$, $S_b$, $S_c$). The transmitted signal propagates along the surface of the earth (a section of which is illustrated in parallelogram 200) in a radial pattern (dotted curves) centered on the transmitter location Tx. If the characteristics of the transmitted signal (e.g., waveform shape parameters and related timing, or magnitude and phase for frequencies of interest) are known, then measurement of the received signal characteristics at receiver $S_c$ will allow calculation of the average electrical conductivity of the soil along the path between the transmitter and receiver, shown as $d_c$ (the distance between the transmitter and receiver $S_c$). If the characteristics of the transmitted signal are not known, then one can determine the average electrical conductivity between two receivers. This is illustrated as the path $d_{ab}$, where the receiver $S_a$ provides the reference characteristics of the signal, and receiver $S_b$ is then used to determine the change in signal characteristics along the path $d_{ab}$.

Electromagnetic fields in the Low-Frequency (LF) and Medium-frequency (MF) range (about 30 kHz to 5 MHz) can propagate hundreds of kilometers over finite-conductivity ground with modest but measurable losses. These losses (for vertical electric fields and horizontal magnetic fields, also known as vertically polarized waves) can be described by an attenuation function and phase shift, and both increase with increasing angular frequency (ω). For a dipole source at height, z, above ground, with a surface conductivity, σ, permittivity, ε, and propagation distance R, the complex attenuation function F is given by:

$$U2(\omega, \sigma) := -\frac{\omega \cdot i}{\omega \cdot i \cdot \varepsilon - \mu_0 \cdot \sigma \cdot c^2} \quad U(\omega, \sigma) := \sqrt{U2(\omega, \sigma)}$$

$$\xi(\omega, R, \sigma) := \frac{\omega \cdot R \cdot U2(\omega, \sigma) \cdot i}{2c} \quad \lambda(\omega, R, \sigma) := \frac{\frac{z}{R} - U(\omega, \sigma)}{\frac{z}{R} + U(\omega, \sigma)}$$

$$F(\omega, R, \sigma) := 1 + i \cdot \left[ \left[ \sqrt{\frac{4 \cdot \pi \cdot \xi(\omega, R, \sigma)}{(1 - \lambda(\omega, R, \sigma))^2}} \cdot \exp\left[\frac{-4 \cdot \xi(\omega, R, \sigma)}{(1 - \lambda(\omega, R, \sigma))^2}\right] \right] \cdot \text{erfc}\left[-i \cdot \sqrt{4 \cdot \frac{\xi(\omega, R, \sigma)}{(1 - \lambda(\omega, R, \sigma))^2}}\right] \right]$$

Figure 3:
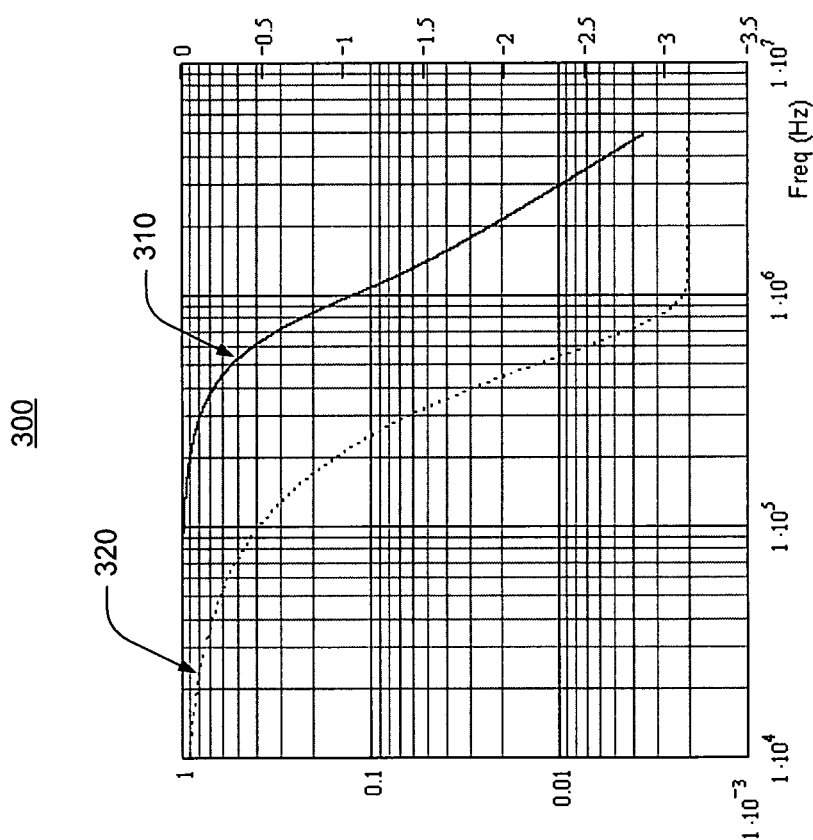
FIG. 3 shows signal attenuation and phase characteristics for an electromagnetic wave propagating along the earth's surface, for one example where conductivity is 10 mS/m and propagation distance is 100 km.

A representative example of the attenuation as a function of frequency 300 is shown in FIG. 3, where the conductivity has been assumed to be 10 mS/m, the propagation distance is 100 kilometers, and the height z=0. The solid curve 310 shows the attenuation (as a fraction of the initial signal amplitude) as a function of frequency, and the dashed curve 320 shows the phase change (in Radians). This function is similar to a two-pole analog low-pass filter whose cutoff frequency is uniquely determined by the ratio σ/R. For this example, the significant conductivity-related changes in attenuation and phase occur in the frequency range of 100 kHz to 1 MHz.

Figure 4A:
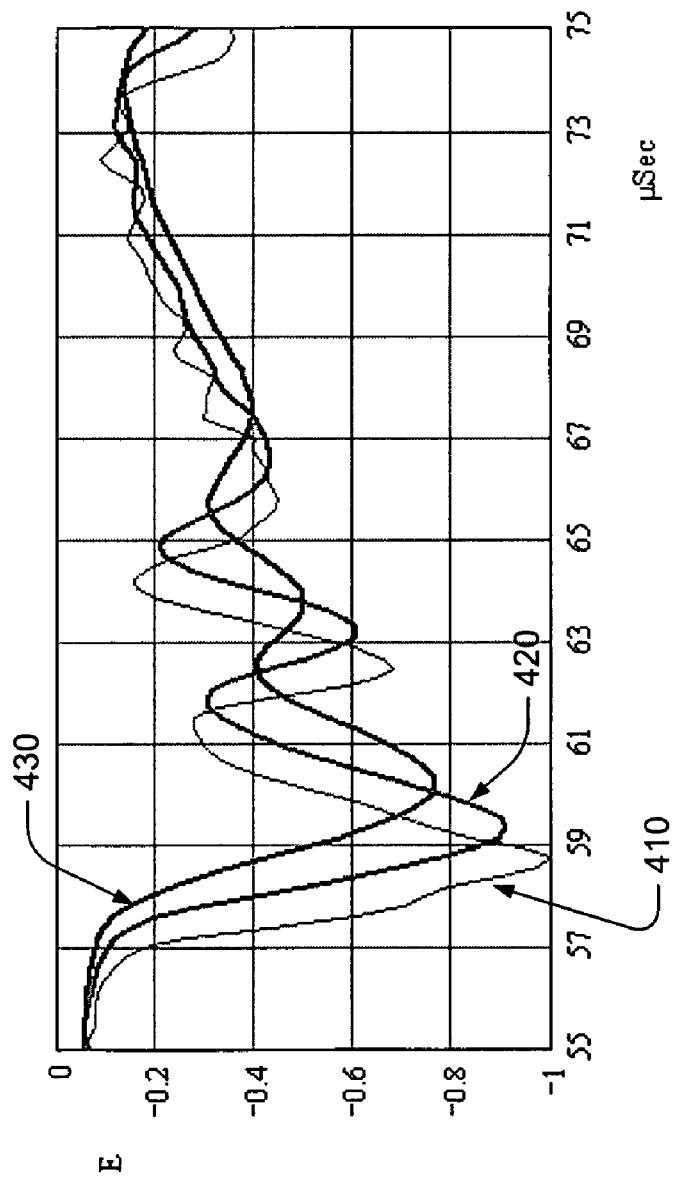
FIG. 4a shows exemplary electric field waveforms for first strokes of negative cloud-to-ground lighting under various propagation conditions.

The signal transfer over a surface, such as the one shown in FIG. 2, 200, produces complicated changes in the initial risetime of a time-domain waveform like that shown in FIG. 4a, 400 which corresponds to the electric field produced by the first stroke of a negative CG lightning flash. Cloud-to-ground lightning flashes are typically identified as either positive or negative polarity, defined by the polarity of the charge effectively lowered to ground. The charge is transferred during (at least) a first return stroke, and frequently during and between one or more subsequent strokes that typically occur with time intervals in the range of 5-200 mS. The horizontal axis shown in FIG. 4a is time (in μs) relative to an arbitrary start time, and the vertical axis is the range-normalized electric radiation field in relative amplitude units. The first waveform 410 illustrates a short (~50 km) propagation distance, so there is very little attenuation below 500 kHz. The second (420) and third (430) waveforms correspond to propagation over a 200 km distance with surface conductivities of 20 and 4 mS/m, respectively. The increasing loss of the high-frequency components under these three conditions creates additional delay, a slower risetime, and a smaller peak amplitude. The tradeoff between a slower risetime and the reduction in amplitude is determined by the duration of the underlying broadband signal—narrow signals will experience a more-significant reduction in amplitude for a given ratio of σ/R, referred to hereafter as the "transfer characteristic." The CG stroke in this particular example is unusually narrow, and this has produced a rather small effect on risetime and a more significant reduction in amplitude with decreasing conductivity.

The propagation effects described above produce real, measurable variations in the risetimes of lightning field waveforms, and the risetime values depend on the surface conductivity. This has been demonstrated using lightning data derived from the U.S. National Lightning Detection Network. One may also use other propagation-related changes in lightning waveform features to track changes in electrical conductivity, all resulting from the transfer characteristics shown in FIG. 3. Examples include an increased delay in arrival time of a transient pulse and an increase in the ratio of peak amplitudes for waveforms recorded by two sensors in different location, both associated with decreasing electrical conductivity.

Figure 4B:
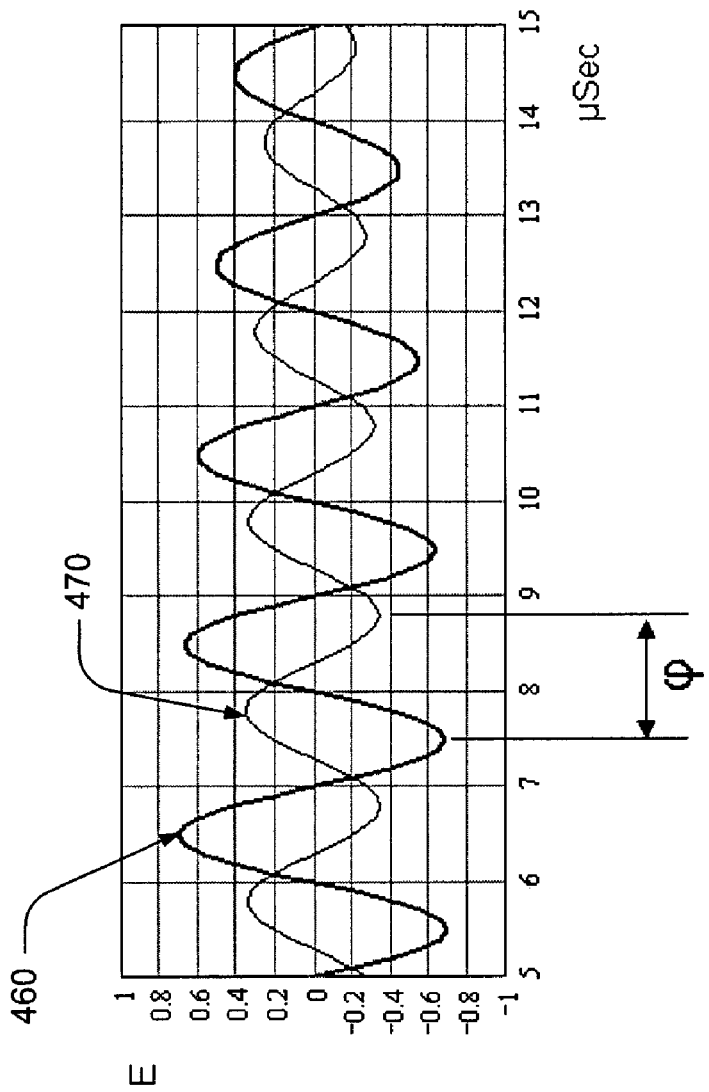
FIG. 4b illustrates exemplary signals produced by an AM transmitter at two propagation distances.

Signals produced by man-made transmitters also exhibit propagation-related changes. The first curve 460 in FIG. 4b is representative of a 500 kHz carrier signal from and amplitude-modulated (AM) signal, measured at a specific distance from an AM transmitter. The signal amplitude scale is arbitrary. The second curve 470 is representative of the signal 460 after propagating an additional 100 km over a path with average conductivity of 10 mS/m. As the diagram 450 shows, the signal has been attenuated by 6 dB, and the phase (φ) has been delayed by approximately 2 radians (corrected for the additional propagation time).

It is known that the depth of penetration of surface-propagated electromagnetic waves is inversely proportional to the square root of frequency and conductivity, with an exemplary penetration depth of about 10 meters at 1 MHz, for an exemplary conductivity of 10mS/m. In alternative aspects of the present invention, different frequencies may be utilized to evaluate conductivity (and therefore moisture) at differing depths.

Aspects of the present invention may provide localized (regional) estimates of soil moisture over a wide area through the arrangement of a plurality of receiving elements used in concert with a plurality of transmitting elements. Soil moisture may be inferred from changes in measured electrical conductivity. The spatial arrangement of sensors may affect the accuracy and spatial resolution of the system.

Figure 5:
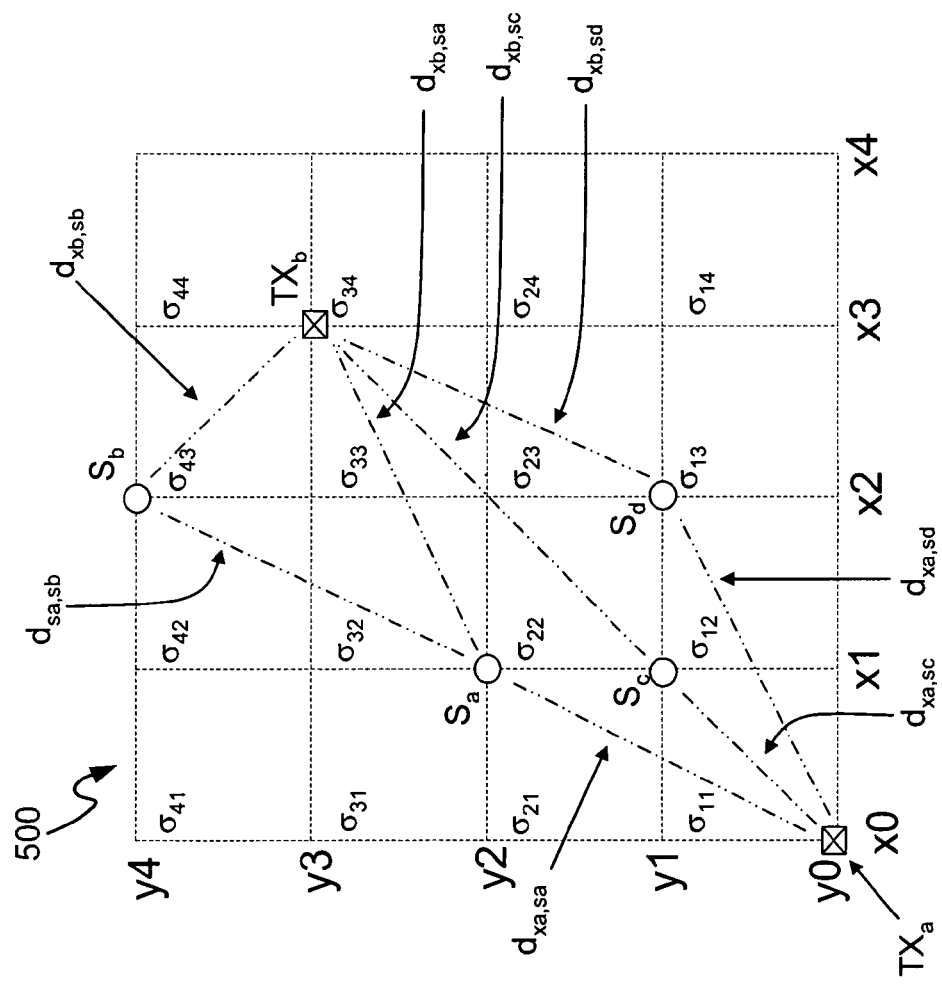
FIG. 5 illustrates an exemplary special arrangement of transmitting and receiving elements.

FIG. 5 illustrates representative arrangements when transmitting elements are in fixed locations. In general, transmitting elements (for example those shown at locations $TX_a$, $TX_b$) and receiving elements (for example those shown at locations $S_a$, $S_b$, $S_c$, and $S_d$) need not be restricted to fixed locations, as long as their locations are known during the measurement of any specific set of signals. In this embodiment, the spatial domain of the system is shown as a regular grid, to facilitate explanation. Transmitting elements (shown at $TX_a$, $TX_b$ small squares with crosses) and receiving elements (shown at $S_a$, $S_b$, $S_c$, and $S_d$ as small circles) are located at intersections of x-y elements in the grid. This network has 25 possible locations, referenced by combinations of (yi, xi), where i is between 0 and 4. The electrical conductivity of the land surface area located between intersecting grid points is represented by a conductivity value $\sigma_{ij}$ (or equivalently a resistively value $\rho_{ij} \cong 1/\sigma_{ij}$). The path length (distance) between any two elements (transmitter-to-receiver or receiver-to-receiver) is represented by $d_{l,m}$, where l and m are two-character symbols whose first character is either an X (transmitter) or an S (receiver/sensor), and the second character is an alphabetic index (a, b, c, ... ). The signal produced by a transmitting element can either have unknown spectral (magnitude and phase) characteristics, or can be "synchronized," meaning that the magnitude and phase characteristics are known, or that the transmitting element is a CG lightning discharge with a fast-rising signal.

In one embodiment, an estimate of conductivity is derived from a single synchronized transmitter and a receiver at the corners of a single grid region, illustrated in FIG. 5 as $\sigma_{11}$. If $TX_a$ is synchronized, then receiver $S_c$ is able to measure the change in the signal over the propagation path. This signal change is either a waveshape change in the time domain, as illustrated in FIG. 4a, or magnitude and phase changes at one or more frequencies, as illustrated in FIG. 3 and FIG. 4b. In either case, the signal change can be uniquely associated with the average electrical conductivity over the known path length ($d_{xa,sc}$, using the propagation characteristics illustrated in FIG. 3. More specifically, the signal change reflects the transfer charact eristic $H_{xa,sc}$ over the path $d_{xa,sc}$ such that $$\sigma_{11} \cong H_{xa,sc} * d_{xa,sc} \tag{1a}$$

where "*" denotes multiplication.

The transfer characteristic (which is proportional to σ/R) can be deduced in a variety of ways, using either the changes in a propagating pulse-like signal (as in FIG. 4a), or in frequency-specific changes in magnitude and/or phase, as shown in FIG. 3 and in FIG. 4b. A specific method for inferring σ/R is described in U.S. Pat. No. 6,961,662 to Murphy et al., (see column 10, lines 40-60), the disclosure of which that is not inconsistent with the disclosure herein is fully incorporated by reference for all purposes.

For mathematical convenience, subsequent formulations will employ electrical resistivity (ρ), which is the reciprocal of electrical conductivity. Equation (1a) can be rewritten in terms of resistivity as follows:

$$\rho_{11} \cong 1/(H_{xa,sc} * d_{xa,sc}) \tag{1b}$$

When the separation between transmitting and receiving elements is longer than the dimension of a single grid, the mathematical expression is more complicated. This is illustrated using the path $d_{xa,sd}$ between $TX_a$ and $S_d$. In this case the effective electrical conductivity over this path is equal to $H_{xa,sd} * d_{xa,sd}$, but this value is comprised of two different conductivities ($\sigma_{11}$, $\sigma_{12}$) that each act on the signal over separate segments of the path $d_{xa,sd}$. The effective resistivity can be represented using a simple distance-weighting, resulting in the equation:

$$(\rho_{11} * \delta(1,1)_{xa,sd} + \rho_{12} * \delta(1,2)_{xa,sd}) \cong 1/(H_{xa,sd} * d_{xa,sd}) \tag{2}$$

Where $\delta(i,j)_{xa,sc}$ is the fraction of the path $d_{xa,sc}$ that is in the (i,j) grid element.

The only unknowns in Equations (1b) and (2) are $\rho_{11}$ and $\rho_{12}$—all other parameters are known from the locations of the transmitting and receiving elements and from the measured transfer characteristics. Given that these form two linear equations with two unknowns, one can solve for the two resistivity values using simple algebra.

In the case where the transmitted or received signals have statistical variability (either due to noise or inherent variability), it may be necessary to average the waveform features over a set of received signals prior to producing the algebraic equations shown in (1b) and (2). In one embodiment, means, medians, or a specific percentile value of parameters are calculated from a set of received signals.

The transfer characteristic between two receiving elements having a common straight-line path to a transmitting element can also be used to determine resistivity. This is illustrated using the path $d_{sa,sb}$ between $S_a$ and $S_d$. In this case $TX_a$ is a common source for both receiving elements. The transfer characteristic $H_{sa,sb}$ can be determined even if $TX_a$ is not synchronized. The equation related to this path is:

$$(\rho_{32} * \delta(3,2)_{sa,sb} + \rho_{42} * \delta(4,2)_{sa,sb}) \cong 1/(H_{sa,sb} * d_{sa,sb}) \tag{3}$$

Following the methodology for expressing relationships among transmitting and receiving elements as presented above, those skilled in the art would understand that similar equations can be written for all combinations of transmitting and receiving elements. The complete set of linear equations can be expressed in matrix notation:

$$[\delta_\rho]/[\rho] \cong [H * d] \tag{4}$$

Where the elements of the vector [H*d] are the reciprocal of the product of the transfer characteristics and the path lengths between selected transmitting and receiving elements, [ρ] is a column vector containing the resistivity values ($\rho_{ij}$) that correspond to the spatial grid regions that are traversed by a path, and [$\delta_\rho$] is a matrix containing the fractional path lengths that are associated with the elements of [ρ].

Note that not all grid elements are traversed by a path (see FIG. 5), and that there may not be enough equations (e.g., at least one per path) to determine the resistivity for all regions traversed by a path. Some of these resistivity values can be estimated using a distance-weighted average of nearest-neighbor resistivity values, and cannot be determined independently.

When CG lightning is employed as the transmitting element, the arrangement of the receiving elements is not dependent on any specific transmitting element locations. In this case, the signal produced by each lightning discharge likely has sufficient energy that it will propagate to receiving elements that are hundreds of kilometers away from the location of the lightning discharge. Since lightning produced by an individual small thunderstorm typically strikes the ground in hundreds of locations as it travels over a distance of 10's to 100's of kilometers, there can be thousands of propagation paths associated with a single storm. Such a large set of measurements will produce an accurate characterization of changes in electrical conductivity with high spatial resolution.

In one exemplary embodiment, it is possible to determine the elements of [ρ] through the following multi-step procedure illustrated in FIG. 7, 700 and as described below. There are other procedures to solve such equations.

Figure 7:
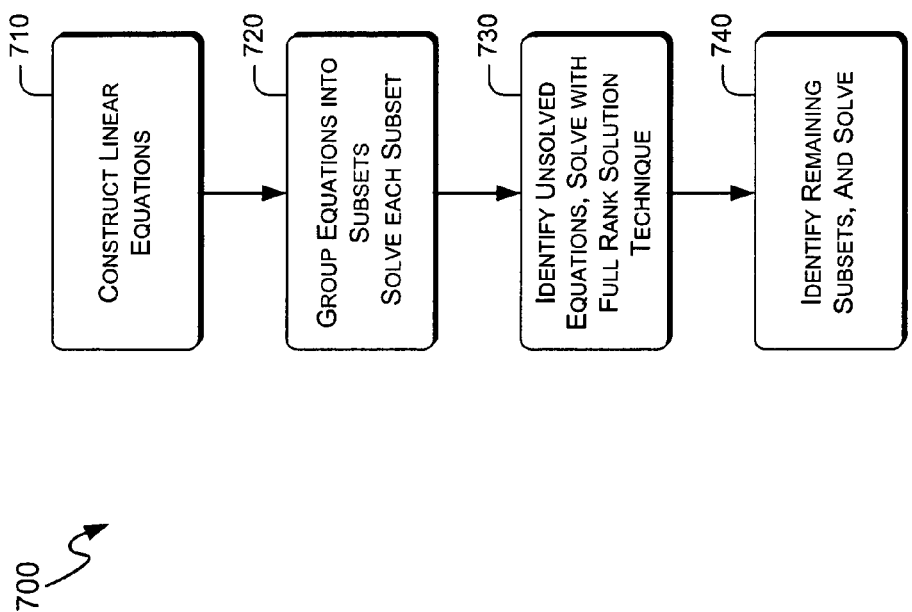
FIG. 7 is a flow diagram describing a process for solving for resistivity values.

Step 1 (FIG. 7, 710). Construct the set of linear equations depicted in Equation (4) using equations (1-3).

Step 2 (FIG. 7, 720). Group together subsets of equations where the number of linearly independent equations is greater than the number of unknown resistivity values (there may be no such sets). Solve these subsets of equations using any technique for solving over-constrained equations, such as the linear least-squared-error method.

Step 3 (FIG. 7, 730). Identify remaining (un-solved) subsets of equations where the number of linearly independent equations is equal to the number of unknown resistivity values (there may be no such sets). Solve these subsets of equations using any technique for solving full-rank equations, such as LU decomposition (Noble and Daniel, 1977).

Step 4 (FIG. 7, 740). Identify remaining (un-solved) subsets of equations where the number of linearly independent equations is one or two less than the number of unknown resistivity values (there may be no such sets). Determine if the number of equations can be augmented to be greater than or equal to the number of unknowns by adding equations where the resistivity in an indeterminable region is expressed as a linear combination of nearest-neighbor resistivity values. Solve these subsets of equations using the approach described in Step 2 or 3, depending on the number of unknowns and linearly independent equations.

Figure 6:
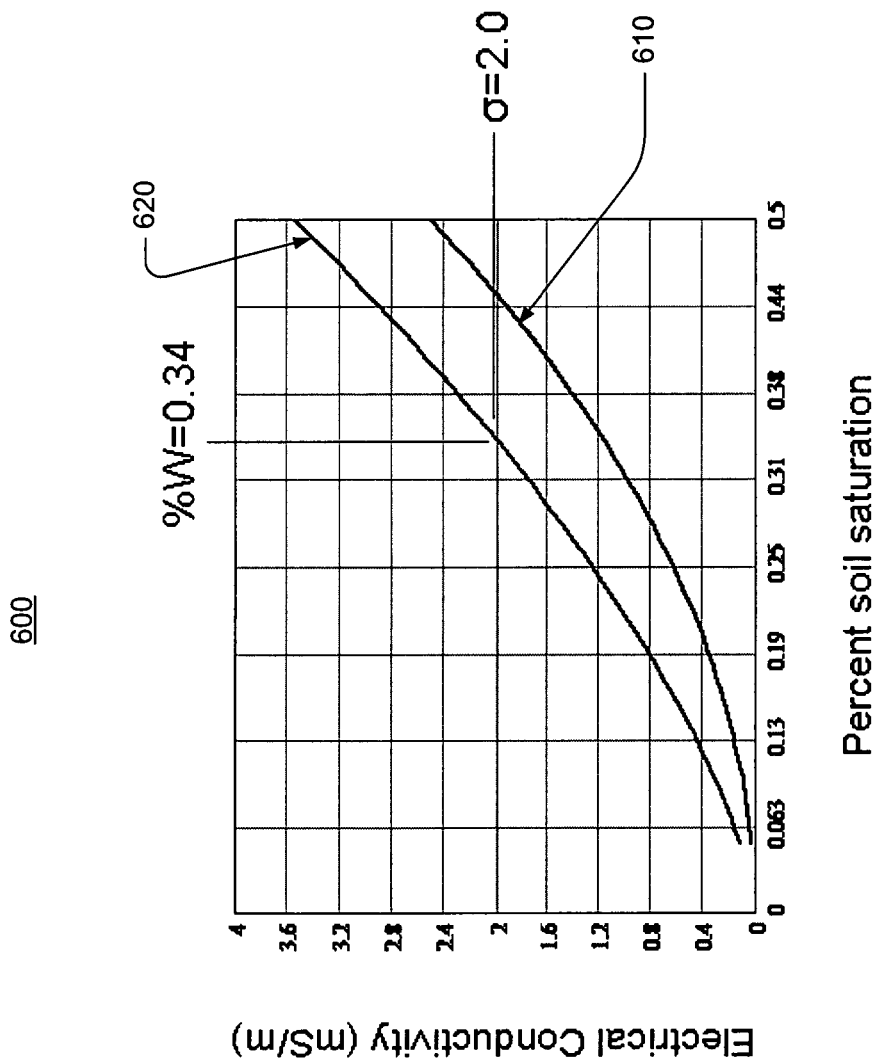
FIG. 6 provides an illustration of electrical conductivity as a function of soil moisture, for two different values of $\alpha$.

Once all possible resistivity values are determined, they are converted to estimated soil moisture in the corresponding region. This is accomplished through knowledge of the soil properties that impact the relationship between electrical resistivity and soil moisture. In this embodiment of the present invention, one form for this relationship known as Archie's Equation may be employed, which shows that electrical conductivity of a specific soil type is proportional to water content:

$$\sigma \cong \frac{\%W^\alpha \cdot \Phi^2}{A \cdot B} = \%W^\alpha \cdot \beta \quad (5)$$

Where $\sigma$ is the electrical conductivity, % W is the percent water content, $\Phi$ is the porosity of the soil, and the parameter $\beta$ represents the relevant soil properties and the resistivity of the water. Different grid points will have different values of $\alpha$ and $\beta$. The exponent $\alpha$ is typically in the range of 1.5 and 2.2. Using this equation, a unique value of % W can be determined for any regional value of conductivity a (reciprocal of resistivity), as illustrated in FIG. 6 for $\beta=10$ and two values of $\alpha$ (1.5 (curve 610) and 2.0 (curve 620)). The proper value of % W is determined by "indexing" into the equation. An example in FIG. 6 shows a percent water content of 0.34 associated with an electrical conductivity of 2.0 mS/m, when $\alpha$ is 2.0.

In general, the relationship between electrical conductivity and soil moisture will depend on soil temperature and soil properties at various depths (top few meters), as well as the moisture saturation at various depths (moisture gradient). Such information is routinely available from existing Land Surface Model (LSM) calculations, such as the NOAH LSM used in the North American Regional Reanalysis. Such information could be used with embodiments of the present invention to refine estimates of soil moisture as a function of depth.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A method for estimating near-surface soil moisture, the method comprising:
   measuring signals from a vertically polarized electromagnetic wave propagating as a ground wave between two or more receiving element locations, the two or more receiving element locations separated from each other by at least one kilometer;
   determining a transfer characteristic proportional to an average electrical conductivity between pairs of locations; and
   determining estimated soil moisture in one or more regions derived from analyzing the determined electrical conductivity between pairs of locations and a predetermined regional relationship between electrical conductivity and soil moisture.

2. The method as disclosed in claim 1, wherein measuring signals from an electromagnetic wave further comprises measuring signals produced by a vertically-polarized radiation-field component of the electromagnetic wave.

3. The method as disclosed in claim 1, wherein the electromagnetic wave is produced by cloud-to-ground lightning.

4. The method as disclosed in claim 3, wherein the transfer characteristic is derived from waveform parameters in the time domain.

5. The method as disclosed in claim 4, wherein a plurality of time-domain parameters is determined from rising edge characteristics of the signals.

6. The method as disclosed in claim 5, wherein the time-domain parameters are the at least one of a peak amplitude, a time delay, and a rise time of the signal.

7. The method as disclosed in claim 3, wherein the transfer characteristic is derived from waveform parameters in the frequency domain.

8. The method as disclosed in claim 1, wherein the electromagnetic wave is produced by a narrow-band transmitter.

9. The method as disclosed in claim 8, wherein the transfer characteristic is derived from waveform parameters in the time domain.

10. The method as disclosed in claim 9, wherein the waveform parameters include at least one of a peak amplitude and a phase delay.

11. The method as disclosed in claim 8, wherein the transfer characteristic is derived from waveform parameters in the frequency domain.

12. A method for estimating near-surface soil moisture, the method comprising:
    measuring signals from a vertically polarized electromagnetic wave propagating as a ground wave produced by one or more man-made narrowband transmitters in the frequency range of 30 kHz 5 MHz at two or more receiving element locations, the two or more receiving element locations separated from each other by at least one kilometer;
    determining a transfer characteristic proportional to an average electrical conductivity between pairs of locations; and
    determining estimated soil moisture in one or more regions derived from the determined electrical conductivity between pairs of locations and knowledge of the regional relationship between electrical conductivity and soil moisture.

13. The method as disclosed in claim 12, wherein the transfer characteristic is derived from waveform parameters in the time domain.

14. The method as disclosed in claim 13, wherein the waveform parameters include at least one of a peak amplitude and a phase delay.

15. The method as disclosed in claim 12, wherein the transfer characteristic is derived from waveform parameters in the frequency domain.

16. A method for estimating near-surface soil moisture, the method comprising:
    measuring signals from an electromagnetic wave propagating as a vertically polarized ground wave produced by one or more return strokes of cloud-to-ground lightning from at least one receiving element location;
    determining a transfer characteristic proportional to an average electrical conductivity between the locations of the lightning and one or more receiving elements;
    determining estimated soil moisture in one or more regions derived from:
       the determined electrical conductivity between a lightning strike location and at least one receiving element location; and
    knowledge of the regional relationship between electrical conductivity and soil moisture.

17. The method as disclosed in claim 16, wherein the transfer characteristic is derived from waveform parameters in the time domain.

18. The method as disclosed in claim 16, wherein a plurality of time-domain parameters is determined from rising edge characteristics of the signals.

19. The method as disclosed in claim 18, wherein the time-domain parameters include at least one of a peak amplitude, a time delay, and a rise time of the signals.

20. The method as disclosed in claim 16, wherein the transfer characteristic is derived from waveform parameters in the frequency domain.

21. A method for estimating near-surface soil moisture, the method comprising:
synthesizing a broadband signal for propagation as a ground wave;
transmitting the synthesized signal from a transmitting element location as a vertically polarized electromagnetic wave coupled to a ground propagation medium at known times;
measuring one or more received signals at one or more receiving element locations separated from each other by at least one kilometer;
determining a transfer characteristic proportional to an average electrical conductivity between pairs of locations; and
determining estimated soil moisture in one or more regions derived from the determined electrical conductivity between the transmitting element location and at least one receiving element location and knowledge of the regional relationship between electrical conductivity and soil moisture.

22. The method as disclosed in claim 21, wherein the transfer characteristic is derived from waveform parameters in the time domain.

23. The method as disclosed in claim 22, wherein the waveform parameters include at least one of a peak amplitude and a phase delay for at least one frequency.

24. The method as disclosed in claim 21, wherein the transfer characteristic is derived from waveform parameters in the frequency domain.

25. The method as disclosed in claim 21, further comprising generating a set of vectors representing a broadband test signal.

26. The method as disclosed in claim 21, wherein the time of transmission of the synthesized signal is not precisely known and two or more receiving elements are employed.

27. The method as disclosed in claim 21, wherein the broadband signal comprises a pseudorandom noise signal.

28. The method as disclosed in claim 21, wherein the broadband signal comprises a broadband Gaussian noise signal.

29. The method as disclosed in claim 25, further comprising controlling broadcast of the broadband signal by specifying at least one of an initial broadcast time, and ending broadcast time, a broadcast repeat interval, and a number of broadcast repetitions.

30. A soil moisture monitoring system comprising:
a data collection and management component coupled to:
one or more RF receiving elements respectively located at one or more receiving element locations, the receiving element locations separated from each other by at least one kilometer; and
an input archive;
a central processing component coupled to:
the data collection and management component;
a product generator for delivering processed information products; and
an output archive; and
a memory coupled to the processing component and storing instructions that, when executed, cause the processing component to:
obtain signals measured from a vertically polarized electromagnetic wave propagating as a ground wave between a transmitter and at least one receiving element location;
determine a transfer characteristic proportional to an average electrical conductivity between the transmitter and at least one receiving element; and
determine estimated soil moisture in one or more regions derived from analyzing the determined electrical conductivity between pairs of locations and a predetermined regional relationship between electrical conductivity and soil moisture.

31. The soil moisture monitoring system as disclosed in claim 30 wherein the data collection and management component is further coupled to:
an RF transmission source comprising the transmitter; and
an input generator, coupled to the RF transmission source and the data collection and management component, the input generator configured to create data for presentation to inputs of the RF transmission source.

32. The soil moisture monitoring system as disclosed in claim 31, wherein the transmission source further comprises one or more transmitting elements that transmit signals at one or more frequencies that can propagate as a ground wave.

33. The method as disclosed in claim 32, wherein the transfer characteristic is derived from waveform parameters in the time domain.

34. The method as disclosed in claim 33, wherein the waveform parameters include at least one of a peak amplitude and a phase delay.

35. The method as disclosed in claim 32, wherein the transfer characteristic is derived from waveform parameters in the frequency domain.

36. The soil moisture monitoring system as disclosed in claim 30, further comprising a transmission source including RF energy produced by one or more return strokes of cloud-to-ground lightning.

37. The method as disclosed in claim 36, wherein the transfer characteristic is derived from waveform parameters in the time domain.

38. The method as disclosed in claim 37, wherein a plurality of time-domain parameters is determined from rising edge characteristics of the signals.

39. The method as disclosed in claim 38, wherein the time-domain parameters include at least one of a peak amplitude, a time delay, and a rise time of the signals.

40. The method as disclosed in claim 36, wherein the transfer characteristic is derived from waveform parameters in the frequency domain.

41. The soil moisture monitoring system as disclosed in claim 30, wherein the electromagnetic wave includes RF sources selected from the group consisting of AM, LORAN, ATC directional beacons, man-made sources of broadband electromagnetic energy, and combinations thereof 42. The method as disclosed in claim 41, wherein the transfer characteristic is derived from waveform parameters in the time domain.

43. The method as disclosed in claim 42, wherein the waveform parameters include at least one of a peak amplitude and a phase delay.

44. The method as disclosed in claim 41, wherein the transfer characteristic is derived from waveform parameters in the frequency domain.

* * * * *